(12) United States Patent
Schneider et al.

(10) Patent No.: US 6,417,197 B1
(45) Date of Patent: Jul. 9, 2002

(54) ACYLATED N-HYDROXY METHYL THALIDOMIDE PRODRUGS WITH IMMUNOMODULATOR ACTION

(75) Inventors: Johannes Schneider, Stolberg; Werner Winter, Aachen; Stephan Wnendt, Aachen; Kai Zwingenberger, Aachen; Kurt Eger, Tuebingen; Michaela Akermann, Eutingen, all of (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 09/155,896

(22) PCT Filed: Mar. 22, 1997

(86) PCT No.: PCT/EP97/01475

§ 371 (c)(1),
(2), (4) Date: Dec. 14, 1998

(87) PCT Pub. No.: WO97/37988

PCT Pub. Date: Oct. 16, 1997

(30) Foreign Application Priority Data

Apr. 9, 1996 (DE) .......................................... 196 13 976

(51) Int. Cl.$^7$ ..................... A61K 31/445; C07D 401/00
(52) U.S. Cl. ....................................... 514/323; 546/201
(58) Field of Search .......................... 514/323; 546/200, 546/201

(56) References Cited

FOREIGN PATENT DOCUMENTS

| DE | 4211812 | * 10/1992 |
| WO | WO 9737988 | * 10/1997 |

* cited by examiner

Primary Examiner—Alan L. Rotman
Assistant Examiner—Binta Robinson
(74) Attorney, Agent, or Firm—Crowell & Moring LLP

(57) ABSTRACT

Thalidomide prodrugs of the formula I:

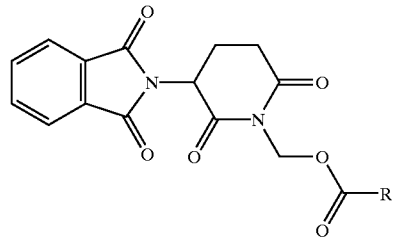

in which R is —CHR$^1$—NHR$^2$ or —(CH$_2$)$_n$COOH; R$^1$ is H or C$_{1-4}$ alkyl; R$^2$ is H, C$_{1-3}$ alkyl, C(O)—CH$_2$—NHR$^3$ or an amino-protective group, R$^3$ is H or an amino-protective group, and n is an integer from 2 to 4, in the form of their free bases or of salts with physiologically acceptable acids, as well as a process for preparation of such prodrugs and the use of such prodrugs as an active drug substance.

10 Claims, No Drawings

ACYLATED N-HYDROXY METHYL THALIDOMIDE PRODRUGS WITH IMMUNOMODULATOR ACTION

BACKGROUND OF THE INVENTION

This invention relates to thalidomide prodrugs, to a method of producing them, and to the use of the same as a pharmaceutical active ingredient.

The excessive formation of the cytokinin TNF-α (tumour necrosis factor α) plays a central part in the pathogenesis of graft-versus-host syndrome, of multiple sclerosis, of transplant rejection, aphthous stomatitis, erythema nodosum leprosum, morbus Boeck, rheumatoid arthritis and a series of other diseases which are associated with inflammatory symptoms. One basis for the therapy of these diseases consists of the targeted suppression of the release of TNF-α, by administering inmmunomodulating active ingredients, such as dexamethasone, pentoxifylline or thalidomide for example.

In the treatment of aphthous stomatitis, thalidomide has proved to be superior to classical immunosuppressants. Other examples of diseases in which thalidomide has exhibited good efficacy without resulting in a general imnmunosuppression include cutaneous lupus erythematosus, pyoderma gangrenosum and orogenital ulcers with morbus Behcet, as well as ulcerations in HIV-infected patients, which do not differ histologically from aphthous ulcers and in which—in contrast to the majority of HIV-associated mucocutaneous lesions—no microbial instigators can be detected. As distinct from stomatitis aphthosa, these lesions, which can be characterised as major aphthae, occur in the entire digestive tract, and when located in the pharyngeal space or the oesophagus make the absorption of food difficult, and also make the taking of oral medication difficult, due to the pain which they cause. The pathogenetic factors are endogenous mediators which have effects on the endothelium and on circulating leukocytes. Under the influence of locally-formed TNF-α and other cytokinins, there is a marked increase in the adhesiveness of the endothelium in relation to leukocytes, which makes a definitive contribution to the development of venous vasculitis. Substances which, like thalidomide, suppress this alteration of the endothelium without at the same time blocking the specific cellular immune defence, can constitute an important advance in therapy.

In severe cases of pharyngeal or oesophageal ulcers, in which the taking of oral medication is made difficult, or in which this may even be impossible, and in cases of HIV-associated pathology in which severe symptoms of diarrhoea make the use of oral medication unpredictable, the parental administration of active ingredients is appropriate. However, the low solubility of thalidomide in water (0.012 mg/ml; Arch. Pharm. 321, 371 (1988)) constitutes an obstacle to the parenteral application of this active ingredient.

Thalidomide derivatives are known from DE 42 11 812 which comprise a benzoyloxymethyl group with an amine-bearing substituent on the nitrogen atom of the glutarimide residue. These thalidomide derivatives have a considerably higher solubility in water than that of thalidomide The pH values of aqueous solutions of these compounds are considerably lower than the physiological pH range, however, so that it is necessary to increase the pH before their application. In the course of this procedure, the corresponding bases are precipitated, with the consequence that the advantage of higher solubility in water is eliminated to a considerable extent or even completely.

SUMMARY OF THE INVENTION

The underlying object of the present invention was to develop thalidomide prodrugs which are water-soluble within the physiological pH range. The object was also that the compounds to be developed should not give rise to any toxicological effects due to the separation of non-physiological prodrug residues.

It has been found that the requirements imposed on the compounds to be developed are fulfilled by selected thalidomide prodrugs.

Accordingly, the present invention relates to thalidomide prodrugs of formula I

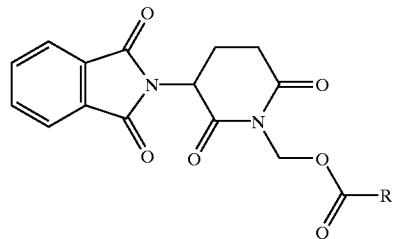

wherein R denotes —$CHR^1$—$NHR^2$ or —$(CH_2)_n COOH$, $R^1$ denotes H or $C_{1-4}$ alkyl, $R^2$ denotes H, $C_{1-3}$ alkyl, $C(O)$—$CH_2$—$NHR^3$ or an amino-protective group, $R^3$ denotes H or an amino-protective group, and n is an integer between 2 and 4, in the form of their bases or salts of physiological acids.

DETAILED DESCRIPTION

The definition of the $R^1$ wherein $R^1$ is a $C_{1-4}$ alkyl radical includes both straight chain and branched hydrocarbon radicals, which may be substituted with OH, COOH, —$C(O)NH_2$, $NH_2$, —$NHC(O)NH_2$, —$NHC(NH)NH_2$ or S—$C_{1-3}$-alkyl, or with a substituted or unsubstituted phenyl group.

The definition of $R^2$ wherein $R^2$ is a $C_{1-3}$ alkyl radical includes straight chain and branched hydrocarbon radicals.

Compounds which are suitable as thalidomide prodrugs of formula I, wherein R denotes —$CHR^1$—$NHR^2$, are those in which the $R^1$ radical denotes H, $CH_3$, —$CH(CH_3)_2$, —$CH_2CH(CH_3)_2$ or —$CH(CH_3)CH_2CH_3$, particularly those compounds in which the $R^1$ radicals denote H, $CH_3$ or —$CH(CH_3)_2$ and $R^2$ denotes H, $CH_3$, $C(O)$—$OC(CH_3)_3$ or $C(O)$—$O$—$CH_2$—$C_6H_5$.

Of the thalidomide prodrugs of formula I in which R denotes —$(CH_2)_n COOH$, the compound in which n is 2 is particularly suitable.

The present invention further relates to a method of producing thalidomide prodrugs of formula I, wherein R denotes —$CHR^1$—$NHR^2$, $R^1$ denotes H or $C_{1-4}$ alkyl, $R^2$ denotes H, $C_{1-3}$ alkyl, $C(O)$—$CH_2$—$NHR^3$ or an amino-protective group, $R^3$ denotes H or an amino-protective group, and $R^3$ denotes H or an amino-protective group, which is characterised in that N-hydroxymethylthalidomide is reacted with an amino acid, the amino function of which is protected, in the presence of a carbodiimide or carbonyldiimidazole, and the protective group for the amino function is subsequently split off by acidolysis if desired.

The t-butyloxycarbonyl radical and the benzyloxycarbonyl radical are particularly suitable as a protective group for the amino function. The reaction of N-hydroxymethylthalidomide with a protected amino acid is conducted in the presence of equimolar to double equimolar amounts of a carbodiimide, for example dicyclohexylcarbodiimide, or of a carbonyldiimidazole, in an organic solvent, for example dichloromethane, chloroform, acetone, dimethylformamide and/or pyridine. The reactions can be conducted in the presence of a catalyst, for example 4-pyrrolidinopyridine or 4-dimethylaminopyridine.

Acidolytic cleavage of the amino-protective group is preferably effected with trifluoroacetic acid, optionally in the presence of an organic solvent, for example dichloromethane.

The present invention also relates to a method of producing thalidomide prodrugs of formula I wherein R denotes $-(CH_2)_n COOH$, which is characterised in that N-hydroxymethylthalidomide is reacted with an acid anhydride in the presence of an amine.

Succinic anhydride is preferably used as the acid anhydride. Triethylamine and/or pyridine are suitable as the amines which are usually used in equimolar to double equimolar amounts with respect to N-hydroxymethylthalidomide. The reactions are usually conducted in an organic solvent, for example dichloromethane, chloroform, pyridine and/or dimethylformamide, in the presence of a catalyst, for example 4-pyrrolidinopyridine or 4-dimethylaminopyridine.

Salts of compounds according to the invention with physiologically compatible acids, for example hydrochloric acid, hydrobromic acid, sulphuric acid, methanesulphonic acid, formic acid, acetic acid, oxalic acid, succinic acid, tartaric acid, mandelic acid, fumaric acid, lactic acid, citric acid, glutamic acid and aspartic acid, are obtainable either from the corresponding bases or from trifluoroacetates. For the production of hydrochlorides, the corresponding trifluoroacetates are preferably converted into hydrochlorides with the aid of a weakly basic anion exchanger. Short chain aliphatic alcohols, for example methanol, are preferred as solvents.

The compounds according to the invention can be applied as substances which are soluble in water in the physiological pH range between 70 and 75, and are toxicologically harmless. Accordingly, the present invention also relates to the use of a thalidomide prodrug of formula I as an active ingredient in drugs, which are preferably administered parenterally.

In addition to at least one thalidomide prodrug of formula I, drugs according to the invention contain support materials, fillers, solvents, diluents, colorants and/or binders. The selection of these adjuvant substances and of the amounts to be used depends on whether the drug is to be administered intravenously, intraperitoneally, intradermally, intramuscularly, intranasally or locally.

The amount of active ingredient to be administered to the patient, which depends on the weight of the patient, on the type of parenteral application, on the indication and on the degree of severity of the illness, is usually between 0.1 and 10 mg/kg of a thalidomide prodrug of formula I.

Due to their pronounced immunomodulatory action, which does not result in a general immunosuppression, thalidomide prodrugs of formula I are suitable for the treatment of all diseases which are characterised by a high level of TNF-α formation or by focal vasculides.

EXAMPLES

Preparation of Compounds According to the Invention t-butyl oxycarbonyl-protected amino acids were prepared by the method described in Hoppe-Seyler's Z. physiol. Chem. 357, 1651 (1976).

Column chromatography separations were performed using silica gel of particle size 0.05–0.2 mm supplied by the Merck company.

The solubility in water was determined by UV spectroscopy at 300 nm and 25° C.

Example 1

N-t-butyl oxycarbonyl-2-aminoacetic acid-[3-(1,3-dihydro-1,3-dioxo-2H-isoindol-2-yl)-2,6-dioxopiperidin-1-yl]methyl ester (1)

2.88 g (10 mmoles) N-hydroxymethylthalidomide, 1.75 g (10 mmoles) N-t-butyl oxycarbonyl-glycine, 206 g (10 mmoles) dicyclohexylcarbodiimide and 0.15 g (1 mmole) 4-pyrrolidinopyridine were stirred in 50 ml of dry dichloromethane for 24 hours at room temperature. The precipitated dicyclohexylurea was subsequently filtered off and the filtrate was shaken first with acetic acid and then with water. After drying the organic phases over magnesium sulphate and removal of the solvent by distillation, the residue was recrystallised from ethanol. 2.59 g (58% theoretical) of compound 1 were obtained, with a melting point of 108 to 111° C.

Example 2

2-aminoacetic acid-[3-(1,3-dihydro-1,3-dioxo-2H-isoindol-2-yl)-2,6-dioxo-piperidin-1-yl]methyl ester hydrochloride (2)

1.78 g (4 mmoles) of compound 1 prepared as in Example 1 were stirred for 1 hour at room temperature in 20 ml of a mixture of 25 volume % trifluoroacetic acid and 75 volume % dichloromethane. The solvent was subsequently removed under vacuum and the residue obtained was co-evaporated with dichloromethane. The trifluoroacetate obtained was in dissolved in 160 ml methanol and was converted into the hydrochloride by means of ion exchange chromatography (Amberlite IR 45, which had previously been converted into the Cl form with 1 N hydrochloric acid, was used as the ion exchanger). After removing the solvent by distillation, the residue obtained was suspended in boiling ethanol and was treated drop-wise with water in order to form a clear solution. 0.81 g (53% theoretical) of compound 2 was obtained, this had a melting point of 227 to 232° C. and a solubility in water of 497 mg/ml, corresponding to 33.6 mg thalidomide/ml.

Example 3

N-t-butyloxycarbonyl-2-methylaminopropionic acid-[3-(1,3-dihydro-1,3-dioxo-2H-isoindol-2-yl)-2,6-dioxo-piperidin-1-yl]methyl ester (3)

4.32 g (15 mmoles) N-hydroxymethylthalidomide, 3.05 g (15 mmoles) N-t-butyl-oxycarbonyl-L-N-methylalanine, 3.09 g (15 mmoles) dicyclohexylcarbodiimide and 0.22 g (1.5 mmoles) 4-pyrrolidinopyridine were stirred in 75 ml dry dichloromethane for 24 hours at room temperature. The precipitated dicyclohexylurea was filtered off and the filtrate was shaken first with acetic acid and then with water. After drying the organic phases with magnesium sulphate, removing the solvent by distillation and purifying the residue by column chromatography using dichloromethane/acetone (in a volume ratio of 9:1), 4.44 g (63% theoretical) of compound 3 with a melting point of 123 to 125° C. were obtained.

Example 4

2-m ethylaminopropionic acid-[3-(1,3-dihydro-1,3-dioxo-2H-isoindol-2-yl)-2,6-dioxopiperidin-1-yl] methyl ester hydrochloride (4)

Compound 3, which was obtained as in Example 3, was converted into compound 4 under the conditions given in Example 2. Crystallisation from methanol/diethyl ether gave 1.05 g (64% theoretical) of compound 4 with a melting point of 147 to 151° C. and a solubility in water of >300 mg/ml, corresponding to >190 mg thalidomide/ml.

Example 5

N-t-butyloxycarbonyl-2-amino-3-methylbutyric acid-[3-(1,3-dihydro-1,3-dioxo-2H-isoindol-2-yl)-2, 6-dioxo-piperidin-1-yl]methyl ester (5)

3.85 g (53% theoretical) of compound 5 with a melting point of 82 to 85° C. were obtained, under the conditions given in Example 3, from 432 g (15 mmoles) N-hydroxymethylthalidomide, 326 g (15 mmoles) N-t-butyloxycarbonyl-L-valine, 3.09 g (15 mmoles) dicyclohexylcarbodiimide and 0.22 g (1.5 mmoles) 4-pyrrolidinopyridine.

Example 6

2-amino-3-methylbutyric acid-[3-(1,3-dihydro-1,3-dioxo-2H-isoindol-2-yl)-2,6-dioxopiperidin-1-yl] methyl ester hydrochloride (6)

1.95 g (4 mmoles) of compound 5 obtained as in Example 5 were converted into compound 6 under the conditions given in Example 2. Crystallisation from ethanol/diethyl ether gave 101 g (60% theoretical) of compound 6 with a melting point of 145 to 150° C. and a solubility in water of >300 mg/ml, corresponding to >190 mg thalidomide/ml.

Example 7

2-(N-t-butyloxycarbonyl-aminomethylcarbonylamino)-acetic acid-[3-(1,3-dihydro-1,3-dioxo-2H-isoindol-2-yl)-2,6-dioxopiperidin-1-yl]methyl ester (7)

3.67 g (73% theoretical) of compound 7 with a melting point of 178 to 181° C. were obtained, under the conditions given in Example 1, from 2.88 g (10 mmoles) N-hydroxymethylthalidomide, 2.32g (10 mmoles) N-t-butyl oxycarbonyl-glycyl-glycine, 2.06 g (10 mmoles) dicyclohexylcarbodiimide and 0.15 g (1 mmole) 4-pyrrolidinopyridine.

Example 8

2-(aminomethylcarbonylamino) acetic acid-[3(1,3-dihydro-1,3-dioxo-2H-isoindol-2-yl)-2,6-dioxo-piperidin-1-yl]methyl ester hydrochloride (8)

1.35 g (77% theoretical) of compound 8 with a solubility in water of >300 mg/ml, corresponding to >190 mg thalidomide/ml, were obtained, under the conditions given in Example 2, from 2.01 g (4 mmoles) of compound 7 prepared as in Example 7.

Example 9

[3-(1,3-dihydro-1,3-dioxo-2H-isoindol-2-yl)-2,6-dioxo-piperidin-1-yl]-methoxycarbonylpropionic acid (9)

2.88 g (10 mmoles) N-hydroxymethylthalidomide, 2 g (20 mmoles) succinic anhydride, 2.8 ml (20 mmoles) triethylamine and 0.15 g (1 mmole) 4-pyrrolidinopyridine were stirred in 50 ml dry dichloromethane for 24 hours at room temperature. The reaction mixture was subsequently shaken firstly with 5% hydrochloric acid and then with water. After drying the organic phases over magnesium sulphate and removing the solvent by distillation, the residue obtained was treated with a small amount of ethyl acetate and the precipitated crystals were recrystallised from ethanol 2.66 g (68% theoretical) of compound 9 were obtained, with a melting point of 143 to 146° C. and a solubility in water of 16.7 mg/ml, corresponding to 11.1 mg thalidomide/ml.

Pharmacological Investigations

The release of TNF-α was investigated in vitro on human mononuclear cells of the peripheral blood (T cells, B cells and monocytes), after stimulation with lipopolysaccharide (LPS). LPS is a constituent of the bacterial cell wall and stimulates monocytes and macrophages.

Mononuclear cells were obtained from the heparin-treated blood of at least three volunteer donors. For this purpose, 20 ml blood in each case were separated by known methods via a Ficoll-Paque gradient, and the cells were harvested and washed three times with a cell culture medium. The cell culture medium which was used consisted of RPMI 1640 medium, supplemented with 2 mM glutamine (Life Technologies, Eggenstein), 10% foetal calf serum (Life Technologies), 50 µg/l streptomycin (Sigma, Deisenhofen), 50 IU/ml penicillin (Sigma, Deisenhofen) and 100 µM β-mercaptoethanol (Merck, Darmstadt). The mononuclear cells were subsequently taken up in 15 ml cell culture medium and were divided into 1 ml batches in sterile 24-hole incubation plates (Sigma) 1 µl dimethylsulphoxide (DMSO, Merck) was added to the 1 ml batches which were used as the control batch. 1 µl of a solution of a compound according to the invention (in DMSO; final concentration in the test: 0.5; 5; 12.5 and 50 µg/ml) was added to the test batches. The batches were incubated for one hour in a $CO_2$ incubation cabinet (5% $CO_2$, 90% atmospheric humidity). 2.5 µg LPS (from *E. coli* 0127: B8, Sigma, Deisenhofen) was subsequently added as a stimulant to each batch with the exception of the control batches. Incubation of the cultures was continued for 20 hours. Following the incubation, the concentration of TNF-α in the cell culture supernatant liquors was determined by ELISA tests (Boehringer Mannheim). The magnitude of the inhibition of the release of TNF-α was calculated from the measured values of the control batches and of the batches incubated with the compounds according to the invention The concentrations which resulted in 50% inhibition of the release of TNF-α (the $IC_{50}$ values) were calculated with the aid of a linear regression line.

The following Table shows the inhibiting effect of the compounds according to the invention on the LPS-induced release of TNF-α

| Compound according to the invention | Inhibition of the release of TNF-α at a final concentration of 50 µg/ml | $IC_{50}$[µg/ml] |
|---|---|---|
| 1 | 78% | 2.7 |
| 2 | 54% | |
| 6 | 97% | 2.0 |
| 9 | 35% | |

Efficacy of Compounds According to the Invention in an Animal Model

For the in vitro characterisation of the immunopharmacological effects of the compounds according to the invention, a test model was selected in which T-lymphocytes were stimulated. The relevance of this immunopharmacological animal model results from the requisite cell-cell cooperation for the initiation of an immune response. The prerequisite for activation and clonal expansion of the T cells is first created by the interaction between antigen-presenting cells, e.g. monocytes, and T cells. This is a characteristic both of defence against infection and of autoimmune aggression or transplant rejection or graft vs. host reaction (graft vs. host disease). Lymphocyte infiltrates constitute the initial stage of chronic graft vs. host reactions, for example, and also constitute the initial stage of acute aphthous lesions in the mucous membrane of the mouth, such as those which occur in morbus Behcet or in what are termed idiomatic aphthae.

The stimulation of T cells was effected by the intravenous application of the staphylococci enterotoxin B (SEB, 200 μg) to balb/c mice which had been pretreated with galactosamine SEB is a superantigen, which firstly binds MHC molecules to antigen-presenting cells, and secondly binds invariable structures to certain T cell-receptor familes. This results in the activation both of T cells and of monocytes. The concentration of the cytokin interleukin-2 (IL-2) in the serum was determined, as a parameter for T cell activation, by means of a commercial ELISA test which specifically detects murine IL-2. The injection of SEB resulted in a time-dependent increase in the serum IL-2 level, with a clear maximum two hours after SEB application The origin of the IL-2 from T cells which was measured in the serum could be verified by the application of SEB to T cell-deficient SCID mice, which thereupon formed no IL-2.

The compounds according to the invention were dissolved in 1% aqueous carboxymethyl cellulose (CMC) and were administered intraperitoneally to the animals, in doses of 100 to 400 mg/kg and in a volume of 1 ml, 30 minutes before the SEB application. The animals of the control group received 1 ml/kg of a 1% aqueous CMC solution, applied intraperitoneally. The serum IL-2 concentrations were determined 2 hours after the application of SEB. The maximum inhibiting effects (in %) on the serum IL-2 level in the groups treated with a compound according to the invention compared with the control group arc given in the following Table. The percentages quoted represent the average values of 6 to 8 separate tests in each case. The doses which resulted in a 40% reduction in serum IL-2 concentrations ($ED_{40}$ values) were calculated via a regression line.

| Compound according to the invention | Max. inhibition of the increase in serum IL-2 at a dose of 400 mg/kg | $ED_{40}$[mg/kg] |
| --- | --- | --- |
| 1 | 34% | |
| 2 | 68% | 230 |
| 4 | 26% | |
| 6 | 52% | |

Comparative investigations showed that, in contrast to glucocorticoids, the compounds according to the invention even inhibited the increase in serum IL-2 when they were administered 30 minutes before stimulation by SEB. To achieve an inhibiting effect by glucocorticoids, however, it was necessary for these substances to be applied 18 hours before stimulation by SEB.

What is claimed is:

1. A thalidomide prodrug corresponding to formula I:

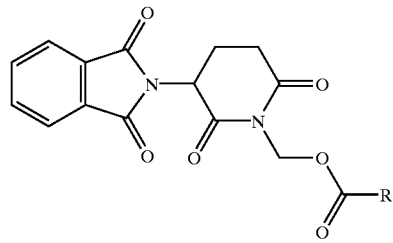

wherein
R denotes —$CHR^1$—$NHR^2$ or —$(CH_2)_n$COOH,
$R^1$ denotes H or $C_{1-4}$ alkyl,
$R^2$ denotes H, $C_{1-3}$ alkyl, C(O)—$CH_2$—$NHR^3$ or an amino-protective group,
$R^3$ denotes H or an amino-protective group, and
n is an integer from 2 to 4,
or a salt thereof with a physiologically acceptable acid.

2. A thalidomide prodrug according to claim 1, wherein $R^1$ denotes H, $CH_3$, —$CH(CH_3)_2$, —$CH_2CH(CH_3)_2$ or —$CH(CH_3)CH_2CH_3$.

3. A thalidomide prodrug according to claim 1, wherein $R^1$ denotes H, $CH_3$ or —$CH(CH_3)_2$ and
$R^2$ denotes H, $CH_3$, C(O)—OC($CH_3$)$_2$ or C(O)—O—$CH_2$—$C_6H_5$.

4. A thalidomide prodrug according to claim 1, wherein n is 2.

5. A method of producing a thalidomide prodrug corresponding to formula I:

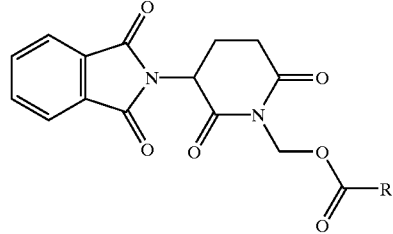

wherein
R denotes —$CHR^1$—$NHR^{21}$,
$R^1$ denotes H or $C_{1-4}$ alkyl,
$R^2$ denotes H, $C_{1-3}$ alkyl, C(O)—$CH_2$—$NHR^3$ or an amino-protective group, and
$R^3$ denotes H or an amino-protective group,
said method comprising the steps of:
reacting N-hydroxymethylthalidomide with an amino acid having an amino function protected by an amino-protective group, in the presence of a carbodiimide or carbonyldiimidazole, and
optionally removing the amino-protective group from the amino function by acid hydrolysis.

6. A method according to claim 5, wherein the amino-protective group protecting the amino function of said amino acid is a t-butyloxycarbonyl or benzyloxycarbonyl group.

7. A method according to claim 5, wherein the amino-protective group is removed by acid hydrolysis with trifluoroacetic acid.

8. A method of producing a thalidomide prodrug corresponding to formula I:

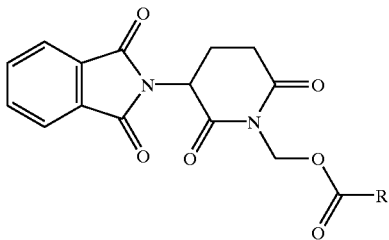

wherein

R denotes —(CH$_2$)$_n$COOH, and n is an integer from 2 to 4, said method comprising the step of reacting N-hydroxymethylthalidomide with an acid anhydride in the presence of an amine.

9. A pharmaceutical composition comprising a pharmaceutically effective amount of a thalidomide prodrug corresponding to formula I:

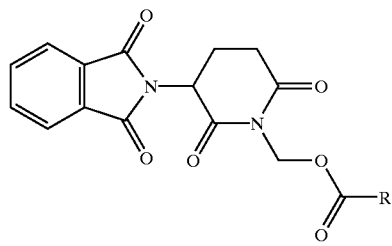

wherein

R denotes —CHR$^1$—NHR$^2$ or —(CH$_2$)$_n$COOH,

R$^1$ denotes H or C$_{1-4}$ alkyl,

R$^2$ denotes H, C$_{1-3}$ alkyl, C(O)—CH$_2$—NHR$^3$ or an amino-protective group, R$^3$ denotes H or an amino-protective group, and n is an integer from 2 to 4, or a salt thereof with a physiologically acceptable acid and at least one pharmaceutically acceptable carrier or adjuvant.

10. A pharmaceutical composition according to claim 9, wherein said carrier is a parenterally administerable solution.

* * * * *